(12) United States Patent
Gray et al.

(10) Patent No.: US 8,424,516 B2
(45) Date of Patent: Apr. 23, 2013

(54) VENTILATING TUBE AND STYLET SYSTEM

(76) Inventors: Terence Kernan Gray, Burlington, CT (US); Gary Steven Sichau, Quincy, MA (US); Niall Patrick Casey, Boston, MA (US)

( * ) Notice: Subject to any disclaimer, the term of this patent is extended or adjusted under 35 U.S.C. 154(b) by 959 days.

(21) Appl. No.: 12/459,594

(22) Filed: Jul. 6, 2009

(65) Prior Publication Data

US 2011/0000485 A1 Jan. 6, 2011

(51) Int. Cl.
*A61M 16/16* (2006.01)
*A62B 23/02* (2006.01)

(52) U.S. Cl.
USPC .............................. 128/203.12; 128/205.12

(58) Field of Classification Search ............. 128/200.26, 128/204.26, 205.19, 205.22, 205.23, 205.24, 128/203.25, 203.12, 205.12
See application file for complete search history.

(56) References Cited

U.S. PATENT DOCUMENTS

| | | | | |
|---|---|---|---|---|
| 3,640,282 A * | 2/1972 | Kamen et al. | ............ | 128/207.15 |
| 4,043,675 A * | 8/1977 | Guennel et al. | ............... | 356/421 |
| 4,244,362 A * | 1/1981 | Anderson | ................ | 128/200.26 |
| 4,637,389 A * | 1/1987 | Heyden | .................... | 128/207.15 |
| 5,546,963 A * | 8/1996 | Doody | ............................ | 128/878 |
| 5,551,946 A * | 9/1996 | Bullard | ......................... | 600/194 |
| 5,595,172 A * | 1/1997 | Reese | ....................... | 128/200.26 |
| 5,685,457 A * | 11/1997 | Liberatore | ..................... | 222/100 |
| 5,810,838 A * | 9/1998 | Solar | ............................. | 606/108 |
| 5,937,860 A * | 8/1999 | Cook | ....................... | 128/207.15 |
| 6,210,315 B1 * | 4/2001 | Andrews et al. | .................. | 600/7 |
| 6,422,239 B1 * | 7/2002 | Cook | ....................... | 128/207.15 |
| 6,427,687 B1 * | 8/2002 | Kirk | ......................... | 128/203.11 |
| 6,892,731 B2 * | 5/2005 | Cook | ........................ | 128/207.15 |
| 7,140,370 B2 * | 11/2006 | Tresnak et al. | .......... | 128/207.14 |
| 7,331,347 B2 * | 2/2008 | Cook | ........................ | 128/207.15 |
| 7,546,166 B2 * | 6/2009 | Michels et al. | ............... | 607/125 |
| 2004/0215301 A1* | 10/2004 | Lokhoff et al. | ............... | 607/116 |
| 2006/0147492 A1* | 7/2006 | Hunter et al. | .................. | 424/426 |
| 2008/0135044 A1* | 6/2008 | Freitag et al. | ............ | 128/200.26 |
| 2010/0312174 A1* | 12/2010 | Hoffman | ......................... | 604/29 |
| 2011/0000485 A1* | 1/2011 | Gray et al. | ............... | 128/203.12 |
| 2011/0259327 A1* | 10/2011 | Wondka et al. | ........... | 128/203.14 |

* cited by examiner

*Primary Examiner* — Stephen Crow
(74) *Attorney, Agent, or Firm* — Niall Casey, Esq.

(57) ABSTRACT

A ventilation system and method with a ventilating tube, a stylet removably disposed within the ventilating tube, and a proximal housing. A proximal housing includes a proximal end that connects to the ventilating tube, a distal end that connects to a ventilating machine, a lumen between the proximal end and distal end, an external wall between the proximal end and distal end, a filter contained within the external wall, surrounding the lumen, and connecting the proximal end and distal end, and a cavity between the filter and the external wall. A proximal housing contains at least one detection element and can be sensitive to carbon dioxide. The same proximal housing contains at least one treatment element to heat, cool, humidify, dehumidify, or provide medication to the lumen of the proximal housing.

22 Claims, 8 Drawing Sheets

VENTILATING TUBE AND STYLET SYSTEM

FIELD OF THE INVENTION

The subject invention relates to medical devices. Specifically, the invention relates to endotracheal ventilating systems.

BACKGROUND OF THE INVENTION

Endotracheal tubes are used to provide reliable ventilation and oxygenation to patients with compromised breathing pathways. If a patient is not ventilating or suffers an airway blockage for four minutes and no oxygen can reach the patient, he or she will likely suffer brain damage; if the blockage continues for eight minutes, the patient will likely suffer brain death through either hypoxic brain damage or cardiopulmonary arrest. In cases where the patient's airway is blocked, the time it takes to establish and secure a reliable airway and restore oxygen flow to the patient's lungs is critical.

Endotracheal tube systems are inserted in a patient's airway to provide a conduit to secure a reliable breathing pattern through a secure pathway. In this manner, after either an attempted or successful direct laryngoscopy, the system is most commonly inserted into the patient's airway through the mouth, past the epiglottis and larynx, and into the trachea. In some cases a stylet is first positioned within the endotracheal tube to provide rigidity or stiffness to the semiflexible endotracheal tube which may assist with proper placement of the endotracheal tube within the trachea and not in the esophagus. If a stylet is used, the medical professional inserts an endotracheal tube over the stylet to add rigidity to the endotracheal tube and facilitate the endotracheal tube placement to the desired location. The stylet is then removed and a sealing cuff is inflated leaving a hollow tracheal tube to provide a secure, patent and unobstructed airway. The cuff is a potential space on the proximal end of the endotracheal tube that seals the airway making the endotracheal tube the only lumen for gas exchange for the patient's pulmonary system. This will also prevent oral or gastric contents from entering the patient's lungs.

This procedure requires many steps and is often met with various obstacles. For instance, the endotracheal tube may be incorrectly positioned within the esophagus. If incorrectly positioned within the esophagus, the patient will not receive sufficient, if any, airflow to the lungs. Therefore, a need exists to provide a system and method for reliably determining if the tracheal tube is correctly placed within the trachea thereby providing an unobstructed pathway to the patient's lungs.

One method of determining proper placement of the endotracheal tube, and therefore allowing for proper ventilation of the patient, is to measure the concentration of carbon dioxide within the exhaled gas. Typically, exhaled carbon dioxide gas from a patient's lungs is between 30 mmHg and 40 mmHg (but can range at times between 20 mmHg and 80 mmHg or higher). If proper endotracheal tube placement and ventilation is achieved, the patient's exhaled gas has a measurable concentration of carbon dioxide. If the endotracheal tube is improperly placed within the esophagus there should be no sustained or significant concentration of carbon dioxide in the exhaled gas. Therefore, there exists a need to reliably and quickly measure the concentration of carbon dioxide within the exhaled gas to ensure proper placement of the tracheal tube and proper ventilation.

BRIEF SUMMARY OF THE INVENTION

It is therefore an object of this invention to provide a new ventilating tube and stylet system and method used for difficult or emergent airway management.

It is a further object of this invention to provide such a system and method which operates to rapidly place and secure placement of the endotracheal tube.

It is a further object of this invention to provide such a system that can be repeatedly positioned into the patient without a need for using another system.

It is a further object of this invention to provide such a system and method which operates to detect and measure the contents of the exhaled carbon dioxide gas to verify placement within the trachea.

It is a further object of this invention to provide such a system and method which operates to treat the inspiratory gas, for example, by modifying the temperature or humidity.

It is a further object of this invention to provide such a system to filter undesired fluids from contacting sensitive detection or treatment elements.

It is a further object of this invention to provide visualization of the detection or treatment elements of the system to detect change in appearance of the elements.

SUMMARY OF THE INVENTION

In accordance with aspects of the present invention, the improved ventilating endotracheal tube and stylet system incorporates a proximal housing that can be used to detect the presence of exhaled carbon dioxide within exhaled gas from the patient. The device can also treat inspiratory gas following placement of the system by a medical professional. The housing attaches to the proximal end of the endotracheal tube and distal end of an ambu bag or ventilating circuit which is typically attached to a mechanical ventilator. Ventilating systems are well known in the prior art and have been disclosed in several patents, including: U.S. Pat. No. 3,640,282 issued to Kamen et al; U.S. Pat. No. 4,244,362 issued to Anderson; U.S. Pat. No. 4,685,457 issued to Donenfeld; U.S. Pat. No. 5,546,936 issued to Virag et al.; and U.S. Pat. No. 7,140,370 issued to Tresnak et al. Each incorporated by reference in its entirety.

In an embodiment, the improved tracheal tube and stylet system includes a removable stylet to add rigidity to the system during insertion into the patient's airway by the medical professional. If used in this manner, the stylet is subsequently removed from the endotracheal tube to provide a clear airway through the tracheal tube which remains in place.

In an embodiment, a proximal housing positioned between the endotracheal tube and ambu bag or ventilating circuit and a ventilating machine provides a medical professional the option of treating (e.g., warming, cooling, moisturizing, demoisturizing, and delivery of medications) the inspired gas on the way to the patient's lungs or sampling the exhaled gas from the patient's lungs to determine if proper placement has been achieved. The elements within the proximal housing must be visible to the medical professional in order to visually detect if a visual change in the element or elements has occurred. The proximal housing can be constructed of a translucent material or with a series of viewing ports to provide visualization of the enclosed elements.

A carbon dioxide detection element is used to sample the exhaled gas to assist in determining if the endotracheal tube is positioned correctly within the trachea to provide appropriate ventilation to the patient. A chemically treated material is typically used in lung ventilation procedures to assist in determining if the patient's exhaled gas contains significant levels of carbon dioxide, indicating proper placement and ventilation. If the exhaled gas, either passing through or in close contact with the material, contains significant levels of carbon dioxide the material turns from one color to another color. Typically the material turns from blue to yellow if significant levels of carbon dioxide are present in the exhaled ventilatory gas. Carbon dioxide detectors used with ventilating systems are well known in the prior art and are disclosed by U.S. Pat. No. 6,427,687 issued to Kirk and U.S. Pat. No. 7,140,370 issued to Tresnak et al., each incorporated by reference in its entirety.

A filter is used to control the exposure of the elements within the proximal housing to contents which may be expelled into the tracheal tube. If the endotracheal tube is incorrectly placed within the esophagus the contents of the stomach can be expelled into the endotracheal tube. Both liquids and solids can be expelled from the stomach, and if not prevented from reaching the detection element by a filter, can cause the detection element to become inactive or produce unpredictable reactions. It is important to shield the detection element from these unwanted contaminants. In instances where the endotracheal tube is incorrectly positioned within the esophagus, damaging stomach contents may flow through the tube and contaminate the filter. If the filter becomes contaminated with these fluids it will not produce a reliable reading in subsequent ventilation cycles. The filter between the lumen of the proximal housing and the elements contained within the proximal housing is used to protect the sensitive elements from exposure to unwanted fluids or debris. This allows the improved endotracheal tube and stylet system to be reused in the event of a misplaced esophageal intubation where the system can subsequently be properly replaced within the trachea. For example, if the endotracheal tube system is incorrectly placed within the esophagus and unwanted fluid or debris is expelled into or through the system, the sensitive elements within the proximal housing will not be compromised. A medical professional can then reposition the same tracheal tube system and reliably confirm proper placement and ventilation using the uncompromised detection element saving both precious seconds and resources.

The filter does not prevent unwanted contents from reaching the proximal end of the proximal housing, but protects elements contained within the proximal housing from exposure to contents within the lumen of the endotracheal tube and proximal housing.

One embodiment of the improved tracheal tube system includes a proximal housing that may contain a carbon dioxide detector. As gas is exhaled from the patient it passes through the filter and into the proximal housing. Within the proximal housing a carbon dioxide detector can be placed to determine if the exhaled gas contains an appropriate level of carbon dioxide. It is understood that there should be only two reliable pathways beyond the oral pharynx. One is the trachea and the other is the esophagus. It is also understood that under normal conditions there should be not sustainably measured carbon dioxide concentration in the esophagus or stomach. However, there are sustained and measurable concentrations from the trachea or lungs. By reading the carbon dioxide detector, a medical professional can determine if the improved tracheal tube system is properly placed within the trachea and not within the esophagus.

In an embodiment the improved tracheal tube system includes a proximal housing that may contain a heating element to raise the temperature of the inspiratory gas to a desired level and a cooling element to lower the inspiratory gas if desired by the medical professional. Typically, the desired temperature of the inspiratory gas is between 35 and 40 degrees Celsius to match the patient's core body temperature. However, this temperature may be adjusted as desired by the medical professional. It is well documented that there is significant heat loss through breathing systems. In operating rooms across the globe anesthesia providers struggle with the balance of increased fresh inspiratory gas flows into the breathing circuit and the heat loss associated with it. This is because the temperature of the fresh inspiratory gas going to the patient is well below normal body temperature. Once in contact with the patient's airway, there is commonly a significant transfer of heat from the patient's lungs to the gas that is then exhaled out of the body. The cycle repeats itself with every breath. The warming element reduces the difference in temperature between the inspired gas and the patient's body temperature, thereby reducing the heat loss. Additionally, heating of the inspiratory gas may be desired to allow for appropriate ventilation and gas exchange between the inspired gas and the patient's circulatory system. The heating element may heat the inspiratory gas using an exothermic chemical reaction or an electronic heating element. Cooling of the inspiratory gas may be desired to lower the patient's body temperature. The cooling element may cool the inspiratory gas using an endothermic reaction, heat exchange, or electronic heating mechanism.

Additionally, the improved tracheal tube system may include a moisturizing or demoisturizing element to moisten or dry the inspiratory gas as desired by the medical professional. Per the medical professional's guidance, the humidity of the inspiratory gas can be modified to provide proper ventilation and exchange between the inspired gas and the patient's circulatory system. The moisturizing element can humidify the air by chemical means or by evaporation of a moisturizing fluid. Similarly, a demoisturizing or dehumidifying element can dry the air by chemical means or by capturing moisture from the lumen of the proximal housing. By providing a moisturizing element within the proximal housing, the medical professional can modulate the humidity of the inspired gas while simultaneously ventilating the patient. There is also an added port proximal to the patient just beyond the filter, to provide a connection for a nebulizing apparatus. This would be used in addition to other uses, for allowing administration of nebulized medications.

BRIEF DESCRIPTION OF THE DRAWINGS

Other objects, features, and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangement of components set forth in the following description or illustrated in the drawings. If only one embodiment is described herein, the claims hereof are not to be limited to that embodiment. Moreover, the claims are not to be read restrictively unless there is clear and convincing evidence manifesting a certain exclusion, restriction or disclaimer.

Figure 1:
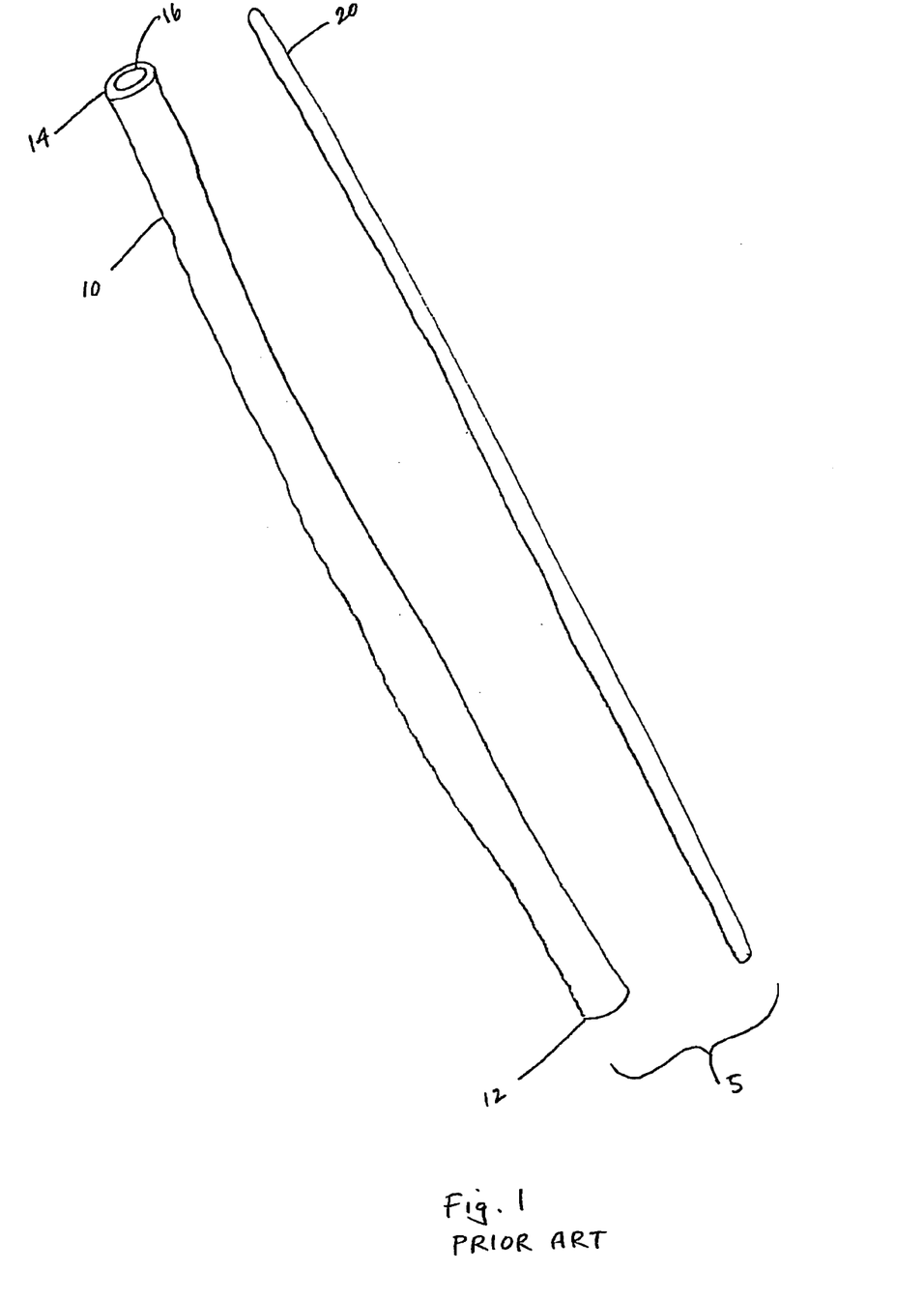
FIG. 1 shows a schematic of the prior art endotracheal tube system.

FIG. 1 shows a schematic of a prior art endotracheal tube system that is typically used by medical professionals to ventilate patients, the system includes an endotracheal tube 10 having lumen 16 that allows gas to flow through endotracheal tube 10. Endotracheal tube 10 has a distal end 12 that is inserted into the patient's airway. Because stylet 20 is more narrow and rigid than tracheal tube 10 it may be first inserted into the patient's trachea. A medical professional then can insert endotracheal tube 10 over stylet 20 and into position within the patient's trachea.

Another method of placing endotracheal tube 10 includes inserting tracheal tube 10 and stylet 20 as a singular assembly into the patient. The rigidity of stylet 20 provides tactile feedback and maintains positioning of endotracheal tube 10 to the medical professional during placement of the prior art endotracheal tube system 5.

Figure 2:
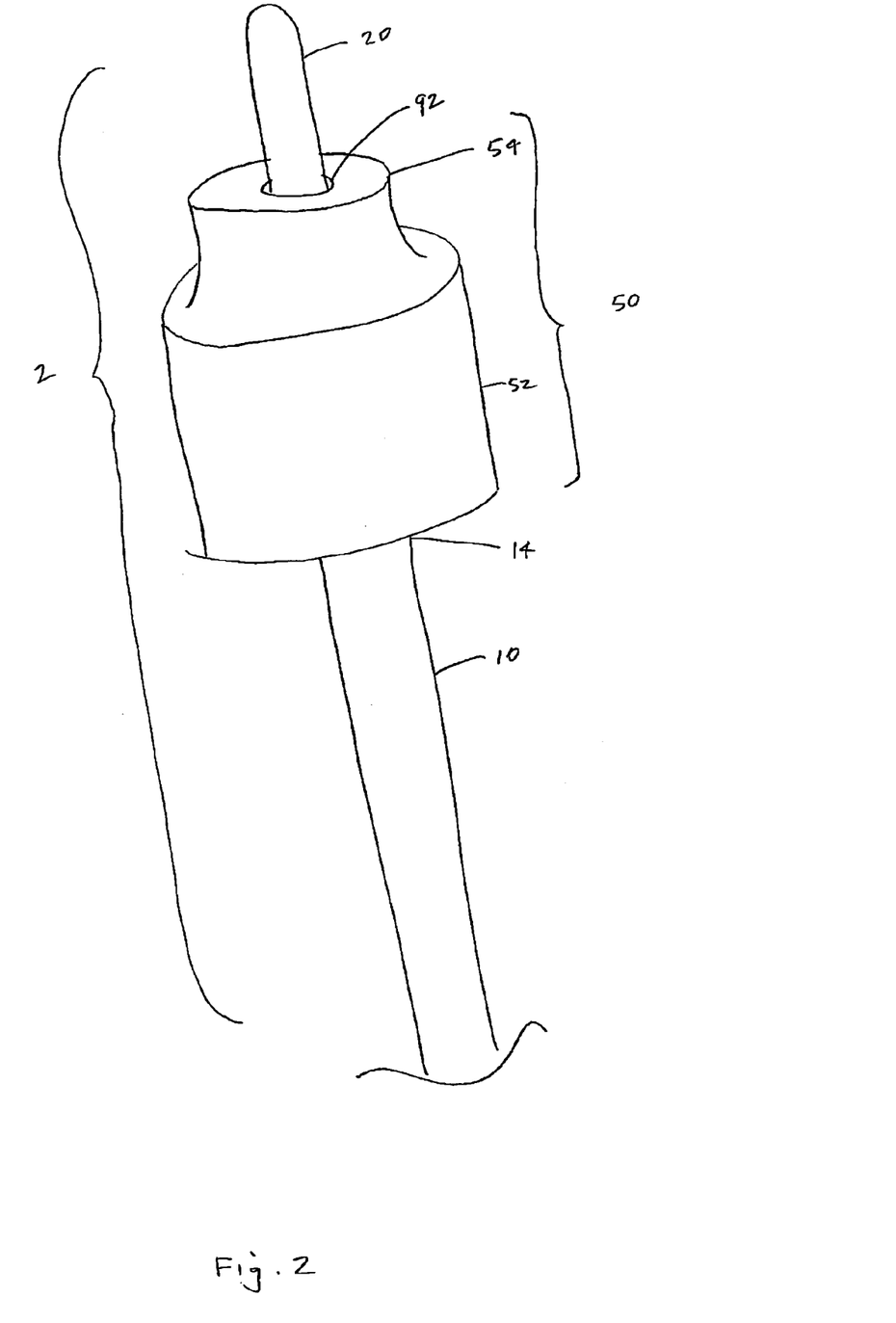
FIG. 2 shows a schematic of the improved endotracheal tube system.
Figure 4:
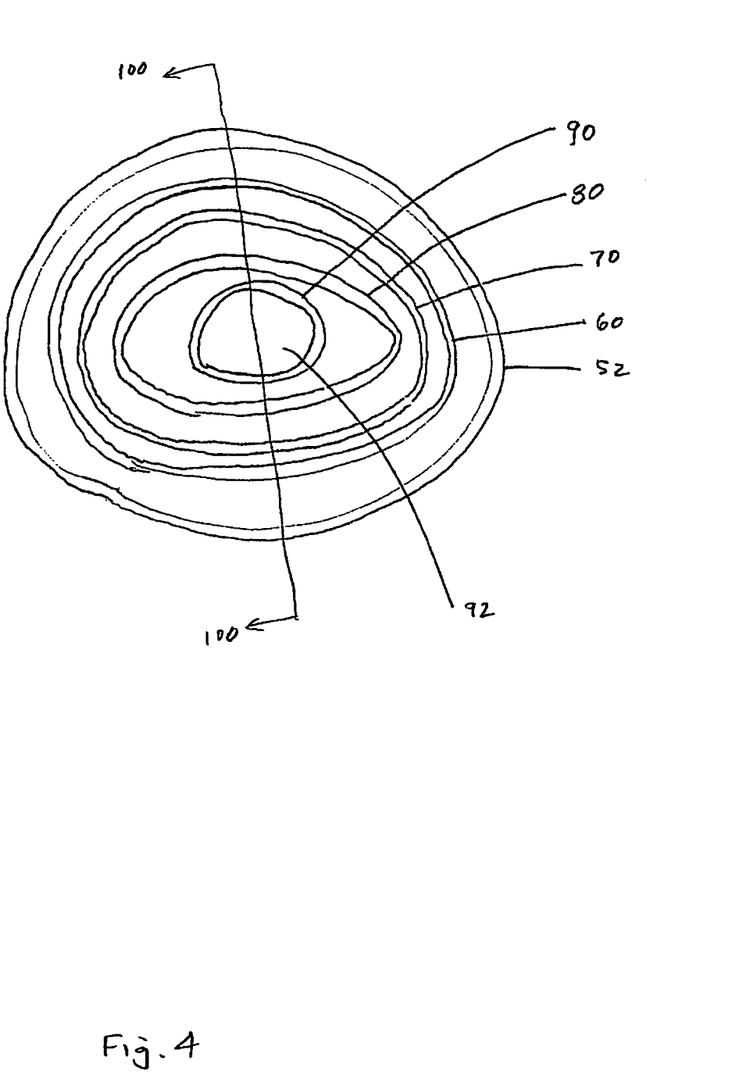
FIG. 4 shows a top view of the proximal housing of the improved endotracheal tube system.
Figure 5:
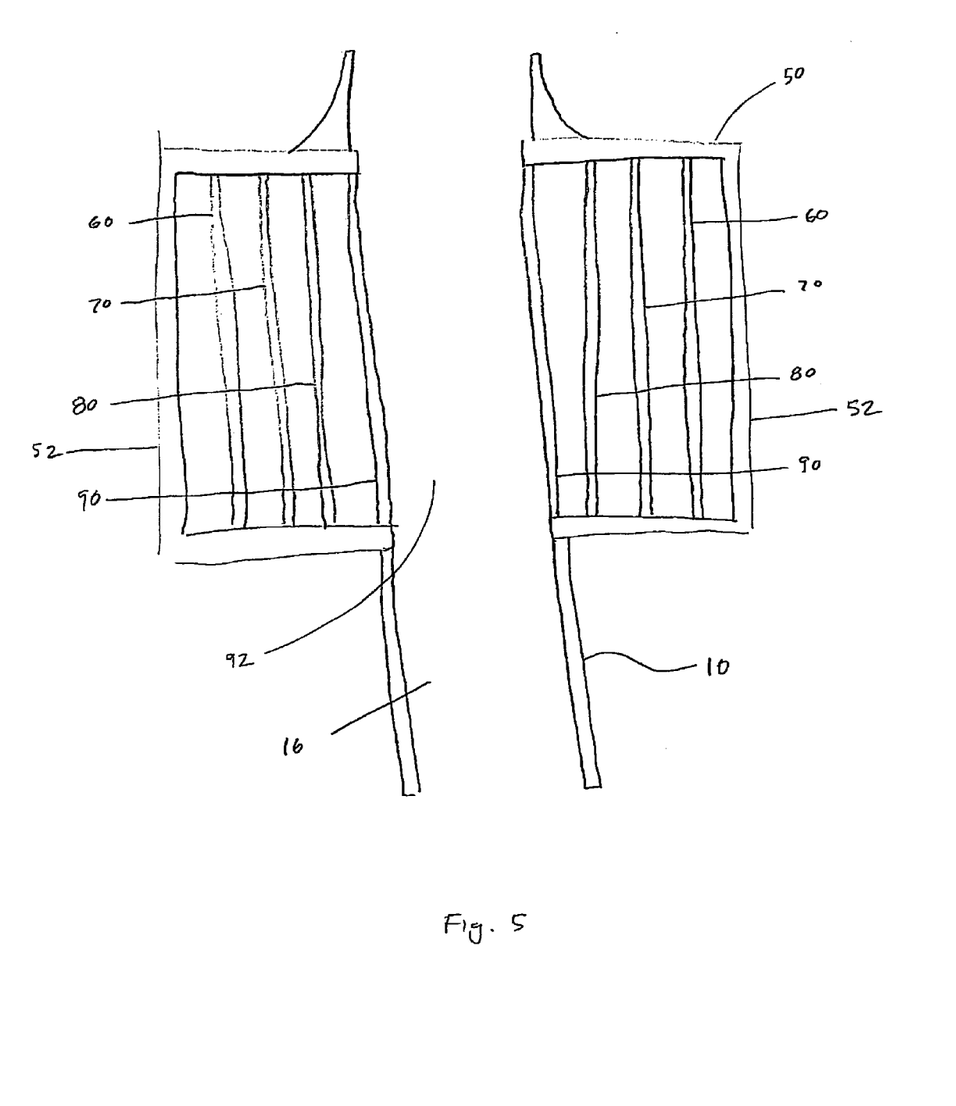
FIG. 5 shows a sectional side view of the proximal housing along line 100-100 of FIG. 4.

FIG. 2 shows a schematic of endotracheal tube system 2 in accordance with aspects of the present invention. Stylet 20 is contained with ventilating endotracheal tube 10 to provide rigidity to endotracheal tube system 2 and tactile feedback to the medical professional responsible for positioning endotracheal tube system 2. At the proximal end 14 of ventilating tube 10 is proximal housing 50. FIG. 5 shows a cross section of proximal housing 50. In this embodiment, external walls 52 enclose the proximal housing 50. Contained within external walls 52 are elements 60, 70, 80, and 90. Proximal housing 50 contains a series of elements 60, 70, 80, and 90, shown in FIGS. 3 through 5, which can filter, monitor, or treat inspiratory or exhaled gas as desired. Lumen 92 shown in FIG. 4 of proximal housing 50 provides a pathway for gas to flow to and from patient's lungs through proximal housing 50. In one embodiment, filter element 90 of FIG. 4 provides a separation barrier between the contents of lumen 16, 92 FIG. 5 and sensitive elements 70, 80, and 90.

If endotracheal tube 10 is incorrectly positioned within the esophagus, vomit or secretions may be forced up endotracheal tube 10 and could contaminate elements 70, 80, and 90 located within proximal housing 50. If secretions and stomach contents come into contact with a sensitive chemical detector used to detect carbon dioxide the detector will become compromised and will need to be replaced. Replacing prior art tracheal tube system 5 consumes valuable time and may cause adverse reactions to the patient including anoxic brain injury or death.

In one embodiment, proximal housing 50 is translucent in order to provide visualization to the contained elements 60, 70, 80, and 90. Detection elements may change color or exhibit another characteristic based on several factors, for example, prior art carbon dioxide detectors change from blue to yellow when exposed to carbon dioxide. Additionally, if an element is used to heat, cool, demoisturize, moisturize, or deliver medications to the inspiratory gas it may change appearance as it looses the ability to heat, cool, demoisturize, moisturize, or deliver medications. Within another embodiment, another modality of visualization uses viewing ports to ascertain if the contained elements have changed in appearance.

As seen in FIG. 2, the improved endotracheal tube system 2 is comprised of ventilating tube 10, removable stylet 20, and proximal housing 50. Proximal housing 50 connects to proximal end 14 of ventilating tube 10 and connects to a ventilating machine via proximal end 54 of proximal housing 50. External wall 52 and lumen 92 of proximal housing 50 enclose a cavity 54, FIG. 4. Cavity 54 houses elements 60, 70, 80, and 90.

Figure 3:
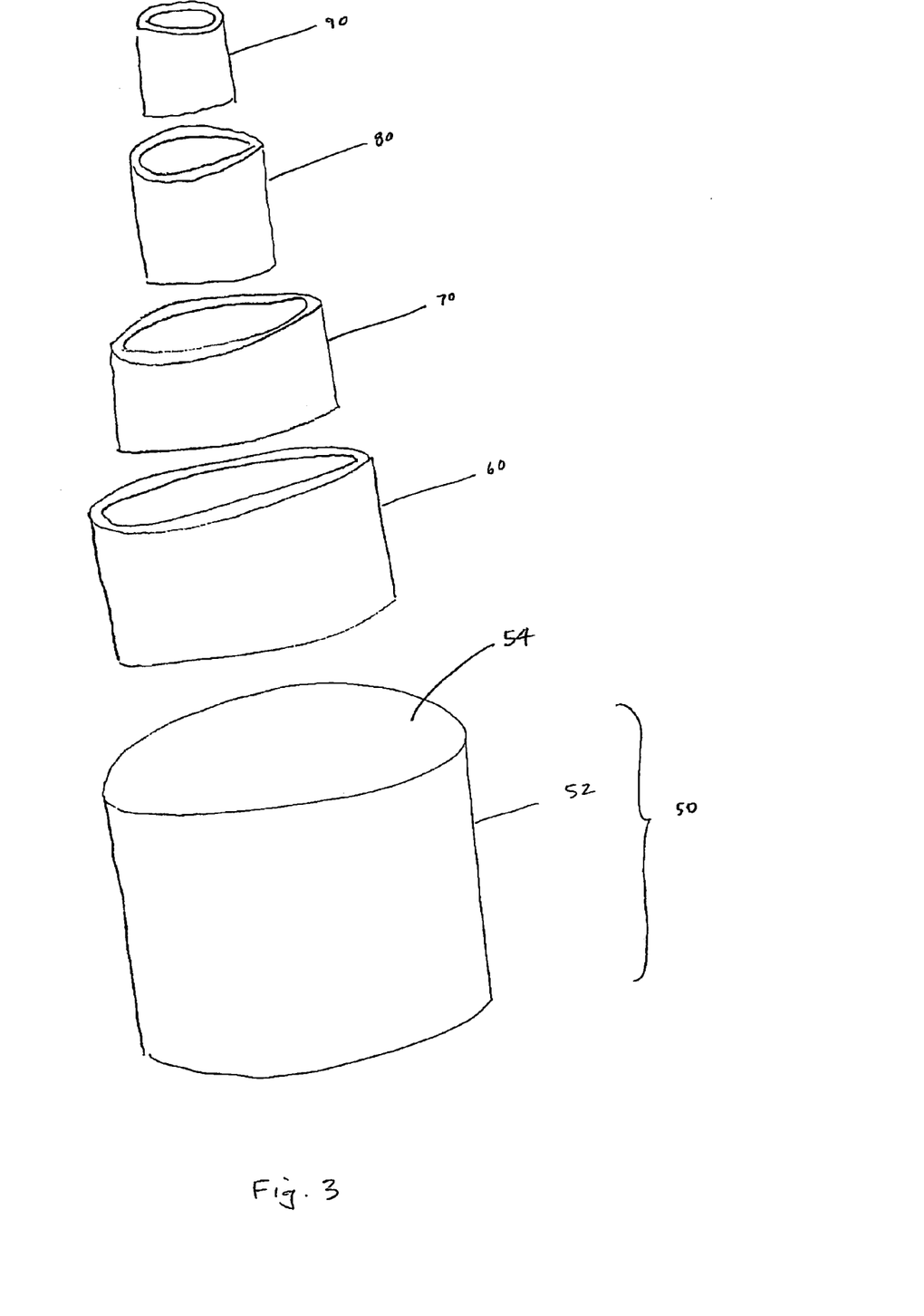
FIG. 3 shows an exploded view of the proximal housing of the improved endotracheal tube system.

FIG. 3 shows an exploded view of the proximal housing of improved endotracheal tube system 2 containing elements 60, 70, 80, and 90. Typically, element 90 is a filter to protect elements 60, 70, and 80 from contamination if undesired fluids travel the length of tracheal tube 10, FIG. 2. The filtering is required because the elements 60, 70, and 80 may not function properly if exposed to undesired fluids. Filter 90, FIG. 3 separates contaminants within lumen 16 and 92 from elements 60, 70, and 80 therefore the medical professional does not have to replace the entire improved endotracheal tube system 2, FIG. 2 if undesired fluid travels up the length of endotracheal tube 10. The medical professional can correctly reposition the improved endotracheal tube system 2 to provide and confirm a satisfactory airway.

Proximal housing 50 and concentric elements 60, 70, 80, and 90 are shown from a top view in FIG. 4. The elements are positioned to allow for the use of a filter. Filter 90 is positioned to separate lumen 92 within proximal housing 50 from elements 60, 70, and 80. Gas flows through lumen 16, FIG. 5 of endotracheal tube 10 and into the contiguous lumen 92 of proximal housing 50. Filter 90 allows gas to pass to elements 60, 70, 80 and protects these elements from undesired fluids or debris that may cause contamination. Section 100-100 from FIG. 4 is shown in FIG. 5 and shows a concentric relationship of elements 60, 70, 80, and 90 arranged around lumen 92 and contained within proximal housing 50.

Any of elements 60, 70, and 80 can be used to detect compounds within the exhaled gas or to treat the inspiratory gas. Element 60, 70, or 80 can be used to detect carbon dioxide within the patient's exhaled gas using a chemically treated material that changes color in the presence of carbon dioxide. In one embodiment, proximal housing 50 is translucent in order for the medical professional to observe a change in color of the elements 60, 70, 80.

Additionally, element 60, 70, or 80 can be used to treat the inspiratory gas as desired by the medical professional. In one embodiment, element 70 can be used to raise or lower the temperature of the inspiratory gas as determined by the medical professional. The heating element may be a package that contains chemicals that are undergoing an exothermic reaction. The exothermic reaction produces heat and warms the inspiratory gas as it flows through lumen 92 of proximal housing 50 into lumen 16 of endotracheal tube 10 and eventually into the patient's lung. An electronic element can also be used raise the temperature of the inspiratory gas to an appropriate level. The inspiratory gas can be cooled using a similar chemical package that contains an endothermic reaction, heat exchange, or an electronic package to lower the temperature of the inspiratory gas.

Element 60, 70, or 80 can be used to raise or lower the humidity of the inspiratory gas. An element can be soaked with a moisturizing compound (such as water) that will add moisture to the inspiratory gas as desired by the medical professional. Or an element can contain a substance that absorbs moisture from the inspiratory gas to dry the gas as it travels to the patient's lungs.

Additionally, element 60, 70, or 80 can be used to provide medication to the patient. If the element contains a medication that can be absorbed by the inspiratory gas the medication can be delivered in an airborne fashion.

Figure 6:
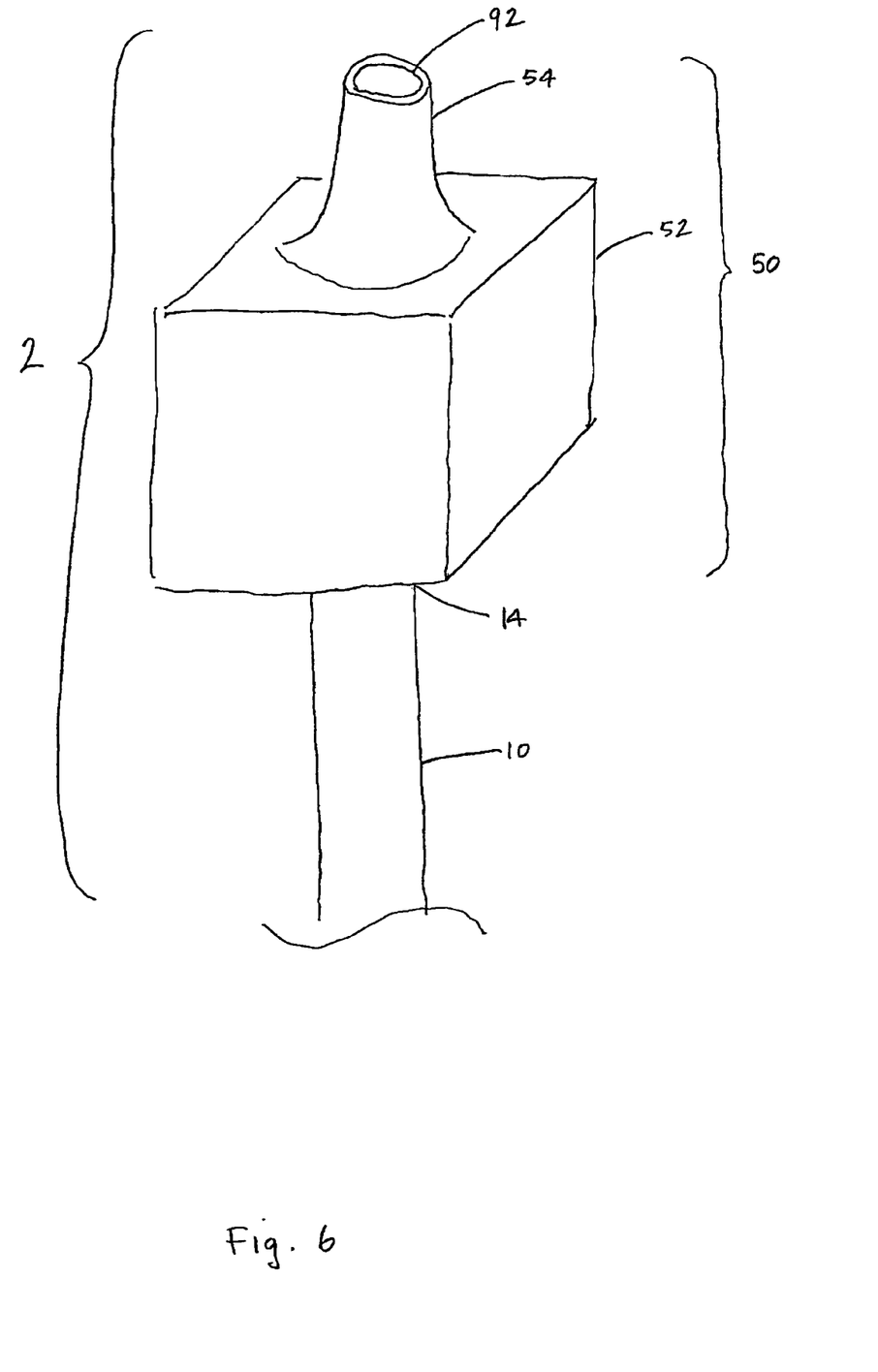
FIG. 6 shows a schematic of another embodiment of the improved endotracheal tube system.
Figure 7:
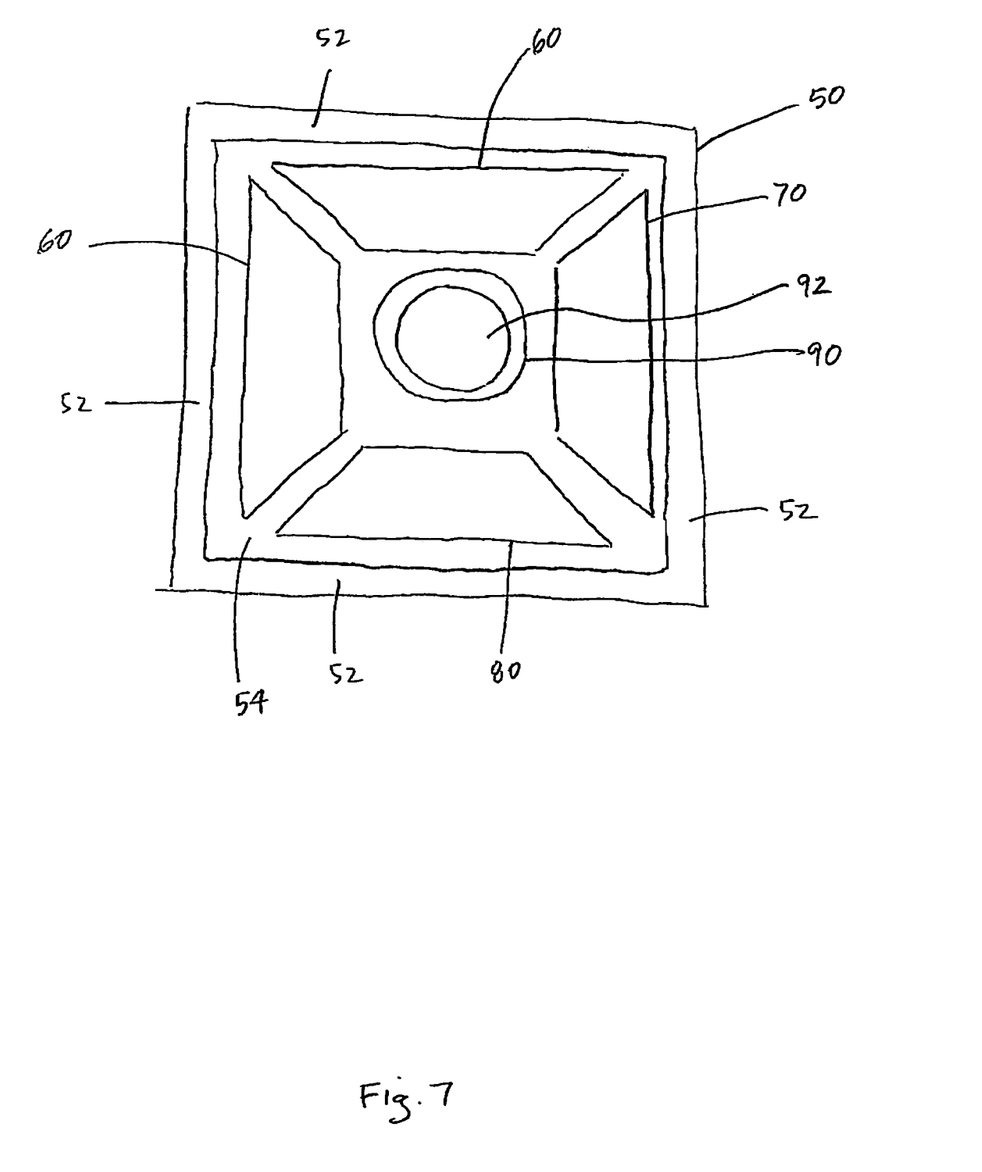
FIG. 7 shows a top view of a cross section of another embodiment of the proximal housing shown in FIG. 6.
Figure 8:
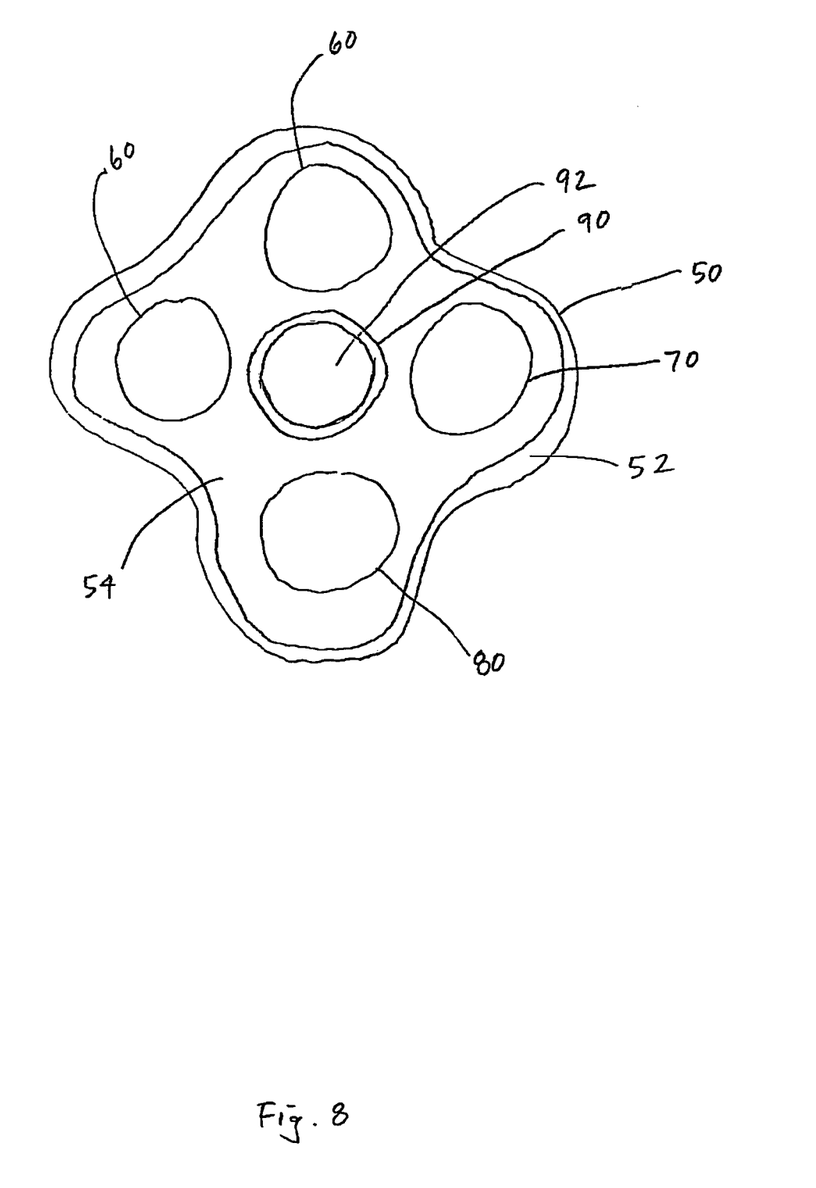
FIG. 8 shows a top view of a cross section of another embodiment of a proximal housing.

In the embodiment depicted in FIGS. 2 through 5 proximal housing 50 is cylindrical and the elements are arranged in a concentric arrangement. In other embodiments, the proximal housing may be configured in other geometries known to those of ordinary skill in the art such as a cube (shown in FIG. 6) or sphere. FIG. 6 shows an embodiment of proximal housing 50 that has a square cross-section. FIG. 8 shows yet another embodiment that has a uniquely shaped cross-section. The geometry of elements 60, 70, and 80 has to fit within cavity 54, (FIGS. 3, 7 and 8) as prescribed by exterior walls 52 of proximal housing 50.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended. Other embodiments will occur to those skilled in the art and are within the following claims.

What is claimed is:

1. A ventilation system comprising:
   a ventilating tube;
   a stylet removably disposed within the ventilating tube; and
   a proximal housing including:
      a proximal end that connects to the ventilating tube;
      a distal end that connects to a ventilating machine;
      a lumen between the proximal end and distal end;
      an external wall between the proximal end and distal end;
      a filter contained within the external wall, surrounding the lumen, and connecting the proximal end and distal end; and
      a cavity between the filter and the external wall; said cavity containing at least one detection element or treatment element.

2. The system of claim 1 where the proximal housing is translucent to provide visualization to the cavity.

3. The system of claim 1 where the proximal housing has viewing ports to provide visualization to the cavity.

4. The proximal housing of claim 1 further comprising said at least one detection element positioned within the cavity.

5. The system of claim 4 where the detection element is sensitive to carbon dioxide.

6. The proximal housing of claim 1 further comprising said at least one treatment element positioned within the cavity.

7. The system of claim 6 where the treatment element raises the temperature of the lumen of the proximal housing.

8. The system of claim 6 where the treatment element lowers the temperature of the lumen of the proximal housing.

9. The system of claim 5 where the treatment element humidifies the lumen of the proximal housing.

10. The system of claim 1 where the treatment element dehumidifies the lumen of the proximal housing.

11. The system of claim 1 where the said at least one treatment element delivers a medication to the lumen of the proximal housing.

12. A ventilation method comprising:
    providing a ventilating tube;
    providing a stylet removably disposed within the ventilating tube; and
    providing a proximal housing, wherein providing the proximal housing comprises:
       connecting a proximal end to the ventilating tube;
       connecting a distal end to a ventilating machine;
       providing a lumen between the proximal end and distal end;
       providing an external wall between the proximal end and distal end;
       providing a filter within the external wall, surrounding the lumen, and connecting the proximal end and distal end; and
       providing a cavity between the filter and the external wall; said cavity containing at least one detection element or treatment element.

13. The method of claim 12 where the proximal housing is translucent to provide visualization to the cavity.

14. The method of claim 12 where the proximal housing has viewing ports to provide visualization to the cavity.

15. The method of claim 12 where the proximal housing further comprises said at least one detection element positioned within the cavity.

16. The method of claim 15 where the detection element is sensitive to carbon dioxide.

17. The method of claim 15 further comprising said at least one treatment element positioned within the cavity.

18. The method of claim 17 where the treatment element raises the temperature of the lumen of the proximal housing.

19. The method of claim 17 where the treatment element lowers the temperature of the lumen of the proximal housing.

20. The method of claim 17 where the treatment element humidifies the lumen of the proximal housing.

21. The method of claim 17 where the treatment element dehumidifies the lumen of the proximal housing.

22. The method of claim 17 where the treatment element delivers a medication to the lumen of the proximal housing.

* * * * *